United States Patent
Chen et al.

(10) Patent No.: US 11,644,440 B2
(45) Date of Patent: May 9, 2023

(54) SHEAR WAVE ELASTOGRAPHY WITH ULTRASOUND PROBE OSCILLATION

(71) Applicant: Mayo Foundation for Medical Education and Research, Rochester, MN (US)

(72) Inventors: Shigao Chen, Rochester, MN (US); James F. Greenleaf, Rochester, MN (US); Armando Manduca, Rochester, MN (US); Daniel C. Mellema, Rochester, MN (US); Joshua D. Trzasko, Rochester, MN (US); Matthew W. Urban, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 508 days.

(21) Appl. No.: 16/637,349

(22) PCT Filed: Aug. 9, 2018

(86) PCT No.: PCT/US2018/045965
§ 371 (c)(1),
(2) Date: Feb. 7, 2020

(87) PCT Pub. No.: WO2019/032803
PCT Pub. Date: Feb. 14, 2019

(65) Prior Publication Data
US 2021/0356434 A1    Nov. 18, 2021

Related U.S. Application Data

(60) Provisional application No. 62/543,698, filed on Aug. 10, 2017.

(51) Int. Cl.
*G01N 29/04*    (2006.01)
*G01N 29/06*    (2006.01)
(Continued)

(52) U.S. Cl.
CPC ....... *G01N 29/043* (2013.01); *G01N 29/0645* (2013.01); *G01N 29/07* (2013.01);
(Continued)

(58) Field of Classification Search
CPC .... G01N 29/043; G01N 29/07; G01N 29/348; G01N 29/42; G01N 29/46; G01N 29/069;
(Continued)

(56) References Cited

U.S. PATENT DOCUMENTS 5,524,636 A    6/1996    Sarvazyan
5,810,731 A *  9/1998    Sarvazyan ........... A61B 5/0093
                                                     600/438
(Continued)

FOREIGN PATENT DOCUMENTS

CN    102151152 A    8/2011
CN    102782518 A    11/2012
(Continued)

OTHER PUBLICATIONS

Complex Empirical Mode Decomposition—An Introduction, IEEE Signal Processing Letters, vol. 14, No. 2, Feb. 2007, Toshihisa et al. (Year: 2007).*

(Continued)

*Primary Examiner* — Jacques M Saint Surin
(74) *Attorney, Agent, or Firm* — Quarles & Brady LLP (57) ABSTRACT

Methods for processing data acquired using ultrasound elastography, in which shear waves are generated in a subject using continuous vibration of the ultrasound transducer, are described. The described methods can effectively separate shear wave signals from signals corresponding to (Continued)

residual motion artifacts associated with vibration of the ultrasound transducer. The systems and methods described here also provide for real-time visualization of shear waves propagating in the subject.

21 Claims, 6 Drawing Sheets

(51) Int. Cl.
*G01N 29/07* (2006.01)
*G01N 29/34* (2006.01)
*G01N 29/42* (2006.01)
*G01N 29/46* (2006.01)

(52) U.S. Cl.
CPC ........... *G01N 29/348* (2013.01); *G01N 29/42* (2013.01); *G01N 29/46* (2013.01); *G01N 2291/02475* (2013.01); *G01N 2291/044* (2013.01); *G01N 2291/0422* (2013.01); *G01N 2291/106* (2013.01)

(58) Field of Classification Search
CPC ......... G01N 29/0645; G01N 2291/044; G01N 2291/0422; G01N 2291/106; G01N 2291/02475; A61B 8/485; A61B 8/5276
USPC ........................................................... 73/620
See application file for complete search history.

(56) References Cited

U.S. PATENT DOCUMENTS

| | | | |
|---|---|---|---|
| 5,983,162 A | 11/1999 | Huang | |
| 6,311,130 B1* | 10/2001 | Huang | G06F 17/14 702/15 |
| 6,329,821 B1 | 12/2001 | Zhou | |
| 6,511,427 B1 | 1/2003 | Sliwa, Jr. | |
| 6,770,033 B1 | 8/2004 | Fink | |
| 6,782,124 B2* | 8/2004 | Gloersen | G06F 17/14 382/207 |
| 7,054,792 B2* | 5/2006 | Frei | G06F 17/14 702/194 |
| 7,444,875 B1 | 11/2008 | Wu | |
| 7,578,789 B2 | 8/2009 | Sandrin | |
| 7,785,259 B2 | 8/2010 | Zheng | |
| 7,975,555 B2 | 7/2011 | Zhuang | |
| 8,532,430 B2* | 9/2013 | Hazard | G01S 7/52042 600/443 |
| 8,602,994 B2 | 12/2013 | Zheng | |
| 8,660,848 B1 | 2/2014 | Humi | |
| 8,734,350 B2 | 5/2014 | Greenleaf | |
| 8,798,399 B2* | 8/2014 | Huang | G06F 17/14 382/302 |
| 8,837,798 B2 | 9/2014 | Li | |
| 10,779,799 B2* | 9/2020 | Chen | A61B 8/485 |
| 10,997,456 B2* | 5/2021 | Vootukuru | G06V 10/48 |
| 11,234,672 B2* | 2/2022 | Yang | A61B 8/485 |
| 2004/0225215 A1 | 11/2004 | Querleux | |
| 2005/0119568 A1 | 6/2005 | Salcudean | |
| 2005/0267695 A1 | 12/2005 | German | |
| 2007/0093716 A1 | 4/2007 | Radulescu | |
| 2009/0182234 A1 | 7/2009 | Perrey | |
| 2009/0304246 A1 | 12/2009 | Walker | |
| 2010/0286516 A1 | 11/2010 | Fan | |
| 2011/0130660 A1* | 6/2011 | Cloutier | A61B 8/5215 600/438 |
| 2011/0201931 A1 | 8/2011 | Palmeri | |
| 2012/0123263 A1 | 5/2012 | Osaka | |
| 2012/0123562 A1 | 5/2012 | Oster | |
| 2012/0215101 A1 | 8/2012 | Maleke | |
| 2012/0226158 A1 | 9/2012 | Greenleaf | |
| 2012/0269414 A1 | 10/2012 | Zha | |
| 2013/0296698 A1 | 11/2013 | Fraser | |
| 2014/0147012 A1 | 5/2014 | Park | |
| 2014/0147013 A1 | 5/2014 | Shandas | |
| 2014/0330122 A1 | 11/2014 | Baghani | |
| 2015/0216507 A1 | 8/2015 | Greenleaf | |
| 2017/0156701 A1 | 6/2017 | Urban | |
| 2017/0333005 A1 | 11/2017 | Chen | |
| 2018/0296191 A1 | 10/2018 | Mellema | |

FOREIGN PATENT DOCUMENTS

| | | |
|---|---|---|
| JP | H08191834 | 7/1993 |
| JP | 2008539005 | 11/2008 |
| WO | 2009140607 | 11/2009 |
| WO | 2012080913 A1 | 6/2012 |
| WO | 2013026141 A1 | 2/2013 |
| WO | 2013160468 | 10/2013 |
| WO | 2014055973 | 4/2014 |
| WO | 2014128182 | 8/2014 |
| WO | 2016067072 A1 | 5/2016 |
| WO | 2016069750 A1 | 5/2016 |
| WO | 2017062553 A1 | 4/2017 |

OTHER PUBLICATIONS

The Synchrosqueezing algorithm for time-varying spectral analysis: Robustness properties and new paleoclimate applications Signal Processing vol. 93, Issue 5, May 2013, pp. 1079-1094, Gaurav et al. (Year: 2013).*
Baghani, A. et al., in "A high-frame-rate ultrasound system for the study of tissue motions," IEEE Trans. Ultrason. Ferroelectr. Freq. Control, 2010; 57:1535-1547.
Bamber, J. et al, "EFSUMB guidelines and recommendations on the clinical use of ultrasound elastography. Part 1: Basic principles and technology," Ultraschall in Der Medizin, vol. 34, pp. 169-184, Apr. 2013.
Bamberger R.H. et al, "A filter bank for the directional decomposition of images: Theory and design," IEEE Trans. Signal Process., vol. 40, p. 11, Apr. 1992.
Barr, R.G. et al, "Elastography Assessment of Liver Fibrosis: Society of Radiologists in Ultrasound Consensus Conference Statement," Radiology, vol. 276, pp. 845-861, Sep. 2015.
Bercoff, J. et al, "Supersonic shear imaging: A new technique for soft tissue elasticity mapping," IEEE Trans. Ultrason., Ferroelectr., Freq. Control, vol. 51, pp. 396-409, Apr. 2004.
Chen, S.G. et al, "Shearwave Dispersion Ultrasound Vibrometry (SDUV) for Measuring Tissue Elasticity and Viscosity," IEEE Trans. Ultrason., Ferroelectr., Freq. Control, vol. 56, pp. 55-62, Jan. 2009.
Daubechies, I. et al. "Synchrosqueezed Wavelet Transforms: an Empirical Mode Decomposition-like Tool."
Huang, N. E. et al, "Applications of Hilbert-Huang transform to non-stationary financial time series analysis," Appl. Stochastic Models in Bus. and Industry, vol. 19, pp. 245-268, Jul.-Sep. 2003.
Huang, N. E. et al, "The empirical mode decomposition and the Hilbert spectrum for nonlinear and non-stationary time series analysis," Proc. of the Royal Soc. of London: Math. Physical and Eng. Sci., vol. 454, pp. 903-995, Mar. 8, 1998.
International Searching Authority, International Search Report and Written Opinion for application PCT/US2018/045965, dated Oct. 24, 2018.
Kasai C., et al., in "Real-time two-dimensional blood flow imaging using an autocorrelation technique," IEEE Trans. on Sonics Ultrason., 1985; 32(3):458-464.
Knutsson, H. et al, in "Local multiscale frequency and bandwidth estimation," Proc. IEEE Int. Conf. Image Process., 1994.
Linderhed A., "Image compression based on empirical mode decomposition," in Proc. of SSAB Symp. Image Anal., 2004, pp. 110-113.
Lu Y. M. et al, "Multidimensional directional filter banks and surfacelets," IEEE Trans. Image Process., vol. 16, pp. 918-931, Apr. 2007.
Manduca, A. et al, "Magnetic resonance elastography: non-invasive mapping of tissue elasticity," Medical Image Anal., vol. 5, pp. 237-254, Dec. 2001.

(56) References Cited

OTHER PUBLICATIONS

Manduca, A. et all, "Image processing for magnetic resonance elastography", Proc. SPIE, vol. 2710, pp. 616-623 1996.
McAleavey, S.A. et al, "Shear-modulus estimation by application of spatially-modulated impulsive acoustic radiation force," Ultrason. Imaging, vol. 29, pp. 87-104, Apr. 2007.
Mellema, D.C. et al, "Probe Oscillation Shear Elastography (PROSE): A High Frame-Rate Method for Two-Dimensional Ultrasound Shear Wave Elastography," IEEE Trans. Med. Imag., vol. 35, pp. 2098-2106, Sep. 2016.
Nightingale, K. et al, "Shear-wave generation using acoustic radiation force: In vivo and ex vivo results," Ultrasound in Medicine and Biology, vol. 29, pp. 1715-1723, Dec. 2003.
Peng, Z.K. et al, "A comparison study of improved Hilbert-Huang transform and wavelet transform: Application to fault diagnosis for rolling bearing," Mech. Syst. and Signal Process., vol. 19, pp. 974-988, Sep. 2005.
Rilling, G. et al, "Bivariate empirical mode decomposition," IEEE Signal Process. Lett., vol. 14, pp. 936-939, Dec. 2007.
Rilling, G. et al, "On empirical mode decomposition and its algorithms," in IEEE-EURASIP workshop on nonlinear signal and image process., 2003, pp. 8-11.
Sadeghi, S. et al. "Ultrasound elastography using empirical mode decomposition analysis." Journal of medical signals and sensors 4.1 (2014): 18.
Salisbury J. I. et al, "Using modern time series analysis techniques to predict ENSO events from the SOI time series," Nonlinear Processes in Geophysics, vol. 9, pp. 341-345, May-Jul. 2002.
Sandrin, L. et al, "Transient elastography: a new noninvasive method for assessment of hepatic fibrosis," Ultrasound Med. Biol., vol. 29, pp. 1705-1713, Dec. 2003.
Sarvazyan, A.P. et al, "Shear wave elasticity imaging: a new ultrasonic technology of medical diagnostics," Ultrasound in medicine & biology, vol. 24, pp. 1419-1435, Nov. 1998.
Song, P. et al., in "Two-dimensional shear-wave elastography on conventional ultrasound scanners with time-aligned sequential tracking (TAST) and comb-push ultrasound shear elastography (CUSE)," IEEE Trans Ultrason Ferroelectr Freq Control., 2015; 62(2):290-302.
Song, P.F. et al, "Comb-Push Ultrasound Shear Elastography (CUSE): A Novel Method for Two-Dimensional Shear Elasticity Imaging of Soft Tissues," IEEE Trans. Med. Imag., vol. 31, pp. 1821-1832, Sep. 2012.
Wang X.J. et al, "Neurophysiological and Computational Principles of Cortical Rhythms in Cognition," Physiological Rev., vol. 90, pp. 1195-1268, Jul. 2010.

Wang, M. et al, "Imaging transverse isotropic properties of muscle by monitoring acoustic radiation force induced shear waves using a 2-D matrix ultrasound array," IEEE Trans. Med. Imag., vol. 32, pp. 1671-1684, Sep. 2013.
Yamakoshi, Y. et al, "Ultrasonic imaging of internal vibration of soft tissue under forced vibration," IEEE Trans. Ultrason., Ferroelectr., Freq. Control, vol. 37, pp. 45-53, 1990.
Yin, M. et al, "Assessment of hepatic fibrosis with magnetic resonance elastography," Clinical Gastroenterology and Hepatology, vol. 5, pp. 1207-1213, Oct. 2007.
Zhao, H. et al, "External Vibration Multi-Directional Ultrasound Shearwave Elastography (EVMUSE): Application in Liver Fibrosis Staging," IEEE transactions on medical imaging, vol. 33, pp. 2140-2148, Nov. 2014.
Azar, R Z, et al. "2-D high-frame-rate dynamic elastography using delay compensated and angularly compounded motion vectors: preliminary results." IEEE transactions on ultrasonics, ferroelectrics, and frequency control 57.11 (2010).
China National Intellectual Property Administration, First Office Action for application 201580059146.6, dated Jul. 3, 2019, with associate translation.
Deffieux, T., et al. "On the effects of reflected waves in transient shear wave elastography." IEEE transactions on ultrasonics, ferroelecliics, and frequency control 58.10 (2011): 2032-2035.
Eskandari, H., et al. "Identifying malignant and benign breast lesions using vibroelastography." 2013 IEEE International Ultrasonics Symposium (IUS). IEEE pp. 25-28, 2013.
European Patent Office Supplementary Search Report for application 16854283.5, dated Jun. 4, 2019, 14 pages.
European Patent Office Supplementary Search Report for PCT/US2015/057825 dated Aug. 9, 2018.
International Search Report and Written Opinion dated Jan. 19, 2016 in connection with PCT/US2015/057825.
International Searching Authority Search Report and Written Opinion for application PCT/US2016/055649, 10 pages, dated Jan. 25, 2017.
Japan Patent Office, Japanese Office Action for application 2017-523369, dated Jul. 2, 2019, with associate translation.
Parajuli, RK, et al. "Shear wave imaging using phase modulation component of harmonic distortion in continuous shear wave excitation." Japanese Journal of Applied Physics 52.7S (2013): 07HF22.
Sandrin, L, et al. "Shear elasticity probe for soft tissues with 1-D transient elastography." IEEE transactions on ultrasonics, ferroelectrics, and frequency control 49.4 (2002): 436-446.
Schiro, A. L. A research platform for ultrasonic elastograpy based targeted prostate biopsy. Diss. University of British Columbia, 2013.

* cited by examiner

SHEAR WAVE ELASTOGRAPHY WITH ULTRASOUND PROBE OSCILLATION

CROSS-REFERENCE TO RELATED APPLICATIONS

This application is a 371 U.S. National Phase application of PCT/US2018/045965, filed Aug. 9, 2018, which claims the benefit of U.S. Provisional Patent Application Ser. No. 62/543,698, filed on Aug. 10, 2017, and entitled "SHEAR WAVE ELASTOGRAPHY WITH ULTRASOUND PROBE OSCILLATION," which is herein incorporated by reference in its entirety.

STATEMENT REGARDING FEDERALLY SPONSORED RESEARCH

This invention was made with government support under DK106957 awarded by the National Institutes of Health. The government has certain rights in the invention.

BACKGROUND

Many ultrasound elastography techniques have been developed, which are capable of obtaining measurements of mechanical properties in an object or tissue, such as in the liver. These methods utilize shear wave propagation speed to quantitatively estimate the stiffness of soft tissue or other materials. For example, for an elastic material, the shear modulus is equal to the square of the shear wave speed times its density (often assumed to be 1000 kg/m$^3$ for soft tissue). For soft tissue, the Young's modulus is approximately three times the shear modulus. For viscoelastic materials, a Voigt model can be used to calculate the elasticity and viscosity of the material from the measured shear wave speed at different frequencies. Similarly, the storage and loss modulus of a material are also related to the shear wave propagation speed. Therefore, these and other mechanical properties can be estimated using ultrasound elastography techniques.

One of the first ultrasound methods capable of making hepatic stiffness measurements was transient elastography ("TE"). This method utilizes a small single-element transducer to deliver a mechanical impulse to generate a transient shear wave. Propagation of the longitudinally polarized shear wave is detected by the same single-element transducer along its beam axis. The resulting one-dimensional (1D) motion profile can be utilized to determine a global shear wave speed value through the use of a time-to-peak method.

More recently, acoustic radiation force ("ARF") has been utilized to generate propagating shear waves with cylindrical wave fronts conducive for 2D ultrasound imaging. ARF-based elastography may use the time-to-peak or time-of-flight method for shear wave speed estimations. While versatile, the ARF technique is limited by ultrasound attenuation and shear wave attenuation. For example, under current FDA regulatory limits the ultrasound push beam used to generate the shear wave has difficulty penetrating beyond 7-8 cm. Even at shallower depths, the resulting shear wave rapidly attenuates, preventing the method from imaging a large 2D area. Another constraint is that scanners must be equipped with specialized hardware and power supplies to generate the high intensity, long duration push pulses, and imaging frame-rates are typically limited to about 1 Hz to prevent excess tissue and probe thermal damage.

Probe oscillation shear wave elastography ("PROSE") has been developed to leverage the increased penetration and coverage of mechanically generated shear waves with the ability to continuously track the motion in 2D. This method generates longitudinally polarized shear waves in the tissue with a monochromatic mechanical vibration of the ultrasound probe. Standard pulse-echo ultrasound detection can then be used to simultaneously track the resulting shear waves while the probe is in motion. Because ultrasound utilizes changes in individual scatterer positions relative to the ultrasound transducer to track motion, the movement of the vibrating transducer between subsequent detections leads to a depth dependent probe motion artifact. The artifact arises as a material compresses when the probe moves through the vibration cycle, with scatterers near the probe moving less (relative to the probe surface) than scatterers further from the probe. This results in a non-linear strain-like artifact, causing a bias in shear wave speed estimates.

SUMMARY OF THE DISCLOSURE

The present disclosure addresses the aforementioned drawbacks by providing a method for ultrasound elastography using a continuously vibrated ultrasound transducer. A continuous vibration is provided to an ultrasound transducer, and the vibration of the ultrasound transducer induces a shear wave in an object. Signal data are acquired from the object using the ultrasound transducer. The signal data are indicative of the shear wave propagating within the object. The signal data are processed using an empirical mode decomposition to extract an intrinsic mode function (IMF) from the signal data. The IMF represents motion of the shear wave in the object that has been separated from probe motion artifacts associated with the vibration provided to the ultrasound transducer. The IMF is then stored as shear wave signal data for later processing or use.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

FIGS. 4A-4D depict a modified empirical mode decomposition of an example input signal into one or more intrinsic mode functions ("IMFs") associated with shear wave motion signals separated from residual motion artifacts associated with the continuous vibration of an ultrasound transducer. In FIG. 4A, an input function generated from a simulated compression is shown as the summation of two sinusoidal shear waves. The top envelope was obtained by fitting a spline through the local maxima. The midpoint of the top and bottom envelopes is shown in each of FIGS. 4A-4D. After subtracting the midpoints from the input signal in FIG. 4A, an estimate of the wave without the compression is shown in FIG. 4B. Because the midpoint is not sufficiently close to zero at all points, the sifting process is repeated. In FIG. 4C the first IMF after sifting is complete compared with the ground truth of the first sinusoid (grey). In FIG. 4D, the second IMF is shown compared the ground truth of the second sinusoid (grey).

DETAILED DESCRIPTION

Described here are systems and methods for processing data acquired using ultrasound elastography, in which shear waves are generated in a subject using continuous vibration of the ultrasound transducer. The systems and methods described here can effectively remove signals corresponding to residual motion artifacts associated with vibration of the ultrasound transducer. The systems and methods described here also provide for real-time visualization of shear waves propagating in the subject.

Figure 1:
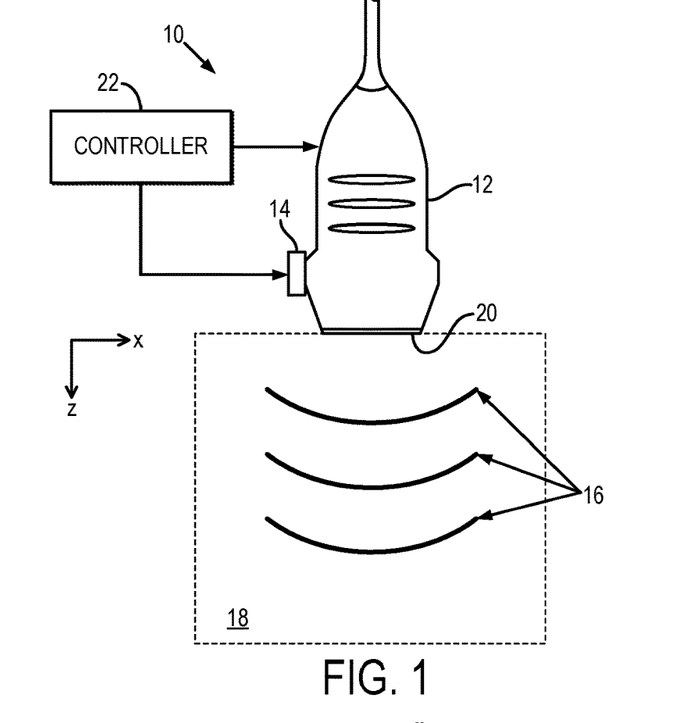
FIG. 1 is a block diagram of an example ultrasound system that implements a continuous vibration of the ultrasound transducer to induce shear waves in an object.

Referring first to FIG. 1, an example system 10 for inducing shear waves in an object 20 is illustrated. In this system, the transducer 12 is mechanically vibrated by an actuator 14, which causes the transducer 12 to oscillate in the axial direction (e.g., the z-direction in FIG. 1). As one example, the actuator 14 can be a mechanical actuator, such as a voice coil actuator. As the transducer 12 moves in the axial direction, shear waves 16 are induced within the object 18. Shear waves 16 can also be produced from mode conversion of compressional waves. The produced shear waves 16 are then detected by the same ultrasound transducer 12 operating in a pulse-echo mode to provide quantitative measurements of mechanical properties of the object.

The transducer 12 and the actuator 14 are operated under the control of a controller 22, which may be implemented, as a computer system, as a microcontroller, with a hardware processor and a memory, or as any other suitable controller hardware and software. In some embodiments, the controller 22 can generate signals for driving the actuator 14. As one non-limiting example, the controller 22 can include a function generator (e.g., Agilent 33250A, Agilent Technologies, Inc., Santa Clara, Calif., USA) that is operated to generate a 30 Hz monochromatic signal, and an amplifier (e.g., Crown D150A, Crown Audio, Inc., Elkhart, Ind., USA; voltage gain: 26 dB) that amplifies the signal generated by the function generator and provides the amplified signal to the actuator 14 in order to drive the actuator 14. The controller 22 can also include hardware and software to receive data from the transducer 12 and process the received data, produce images, compute mechanical properties, or generate other data.

The actuator 14 is coupled to the ultrasound transducer 12. As one example, the actuator 14 can be attached directly to the outer surface of the transducer 12. For illustration purposes, the actuator 14 is attached to one side of transducer 12 in FIG. 1. In some applications, however, it may be preferred to align the actuator co-axially with the transducer 12 so that the transducer motion is primarily axial with minimal elevational (y-direction in FIG. 1) and azimuthal (x-direction in FIG. 1) motions. This setup eliminates the need for a separate vibration source, and therefore allows for a convenient single-handed operation. The vibration is preferably continuous to allow continuous updating of measurements.

The ultrasound transducer 12 can be vibrated axially along the beam axis of ultrasound, or in other directions depending on the desired imaging application. The ultrasound system used for shear wave detection can be operated to detect a single A-line, multiple A-lines through parallel beam forming, or an entire 2D area or 3D volume with plane wave imaging and software beam forming, such as is done in a Verasonics® ultrasound scanner.

The continuous vibration applied to the ultrasound transducer 12 by the actuator 14 can contain multiple frequencies, and the detected shear waves can thus be processed to resolve frequency dependent properties of the object. For example, the processing may use a Fourier transform along the time dimension to select only one frequency at a time, and the subsequent processing would be identical to that as if data were collected with a single vibration frequency. Other processing techniques could also be used, such as those using filters such as bandpass or other filters. Multi-frequency vibrations can speed up acquisition for wave velocity dispersion analysis. With continuous vibration and continuous shear wave detection and processing, elastography measurements can be updated continuously in a substantially real-time manner.

When the transducer 12 is vibrating in the axial direction, such as when the vibration is normal to the active surface 20 of the transducer 12, the motion of the transducer 12 will contaminate the shear wave signals detected in the object 18. This signal contamination is present because ultrasound motion detection uses the transducer 12 as a non-moving reference coordinate, but this assumption is violated when the transducer 12 is oscillating due to external vibration. Therefore, motion of the transducer 12 that is caused by the actuator 14 needs to be corrected for in order to properly measure mechanical properties from the detected shear waves.

Figure 2A:
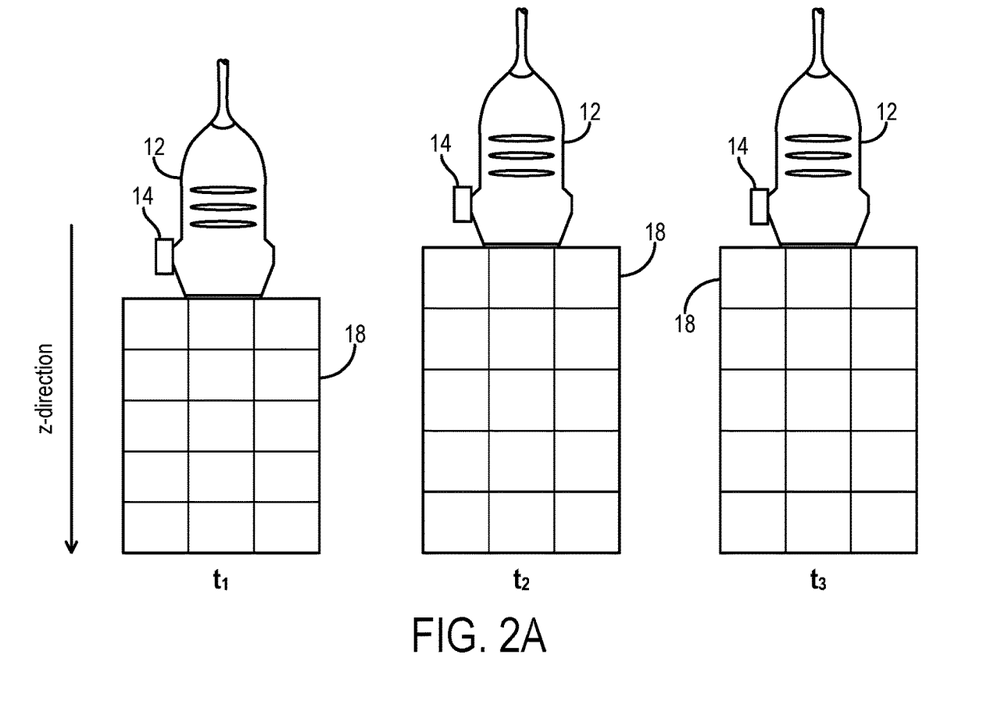
FIG. 2A illustrates a continuously moving ultrasound probe causing different deformations in an object at multiple different time points.
Figure 2B:
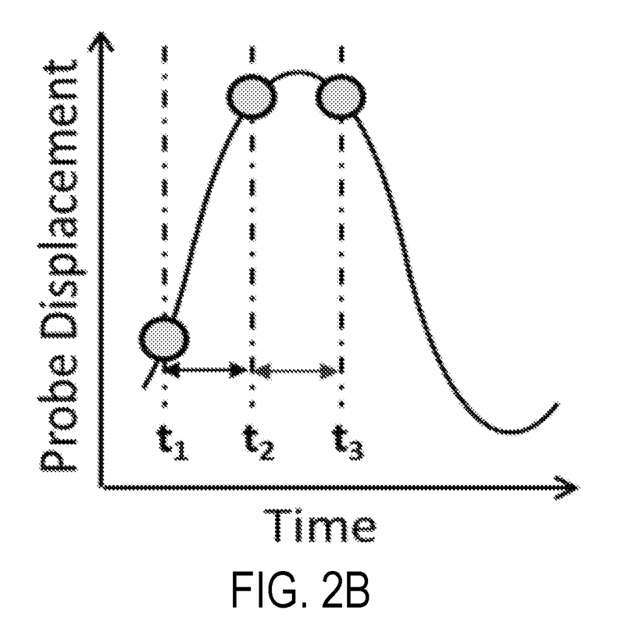
FIG. 2B depicts pulse-echo ultrasound detections of relative motion between different pulse-echo events.
Figure 2C:
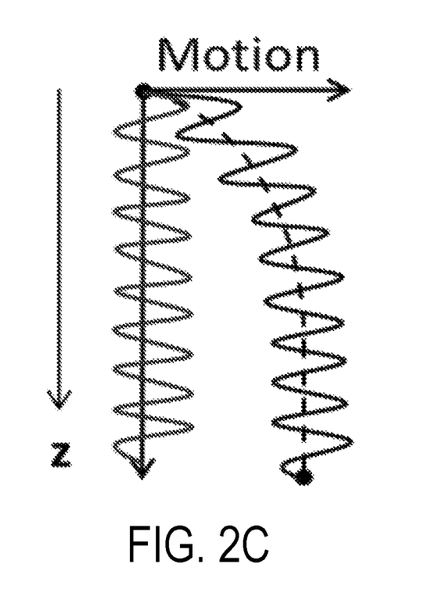
FIG. 2C illustrates that when detections are made when the ultrasound probe is at different physical locations for two pulse-echo events that a resulting strain-like probe motion is observed.

As shown in FIGS. 2A-2C, a continuously moving ultrasound transducer probe causes different deformations in the interrogated material at each time point. As shown in FIG. 2B, pulse-echo ultrasound detects relative motion between two pulse-echo events. If detections are made when the probe is at separate physical locations (e.g., t1-t2), a resulting strain-like probe motion artifact is observed, as shown by the right line in FIG. 2C. If detections are made when the probe has returned to the same location (e.g., t2-t3 in FIG. 2B), it is possible to suppress the artifact, as shown by the left line in FIG. 2C.

The probe motion artifact can thus be suppressed by symmetric sampling, which strategically selects the timing of detections when the probe returns to the same location, minimizing any difference in scatterer position due to material compression, and retaining the motion from the shear waves. This method implements detections with single frames twice per vibration cycle, preventing shear wave speeds from being estimated with time-to-peak or phase gradient methods, which typically requires multiple detections over a vibration cycle. However, the motion was generated with a single tone vibration source, allowing the use of a local frequency estimation ("LFE") on a single frame to estimate the shear wave speeds. As one example, the LFE method described by H. Knutsson, C. F. Westin, and G. H. Granlund, in "Local multiscale frequency and bandwidth estimation," *Proc. IEEE Int. Conf. Image Process.,* 1994, could be used.

While applying PROSE to in vivo cases, the symmetric sampling method may not be able to suppress all of the residual motion that can be caused by out-of-plane waves, reflections, and anatomical motion of the subject. The addition of residual motion violates the underlying assumption that for at any spatial location there exists a single spatial frequency that is related to the mechanical properties if the vibration source is monochromatic. This results in biased shear wave speed estimates. While a spatial bandpass filter can be used to suppress the residual motion, the reconstructed shear wave speed depends on the cutoff values of the bandpass filter.

To produce accurate shear wave speed estimates that are invariant to the filtering process, other means for removing the residual motion are thus desired. The methods described in the present disclosure implement a modified empirical mode decomposition ("EMD") as a non-parametric approach to separate signals into components corresponding to distinct spatial frequencies, allowing the shear wave signal to be decoupled from artifacts and other motion. The methods described in the present disclosure thus allow PROSE to overcome the previous challenges of acquiring motion from only two symmetric frames per cycle, and provide stable shear wave speed estimates in large field-of-view frames at the regular imaging frame rate of the ultrasound scanner.

Figure 3:
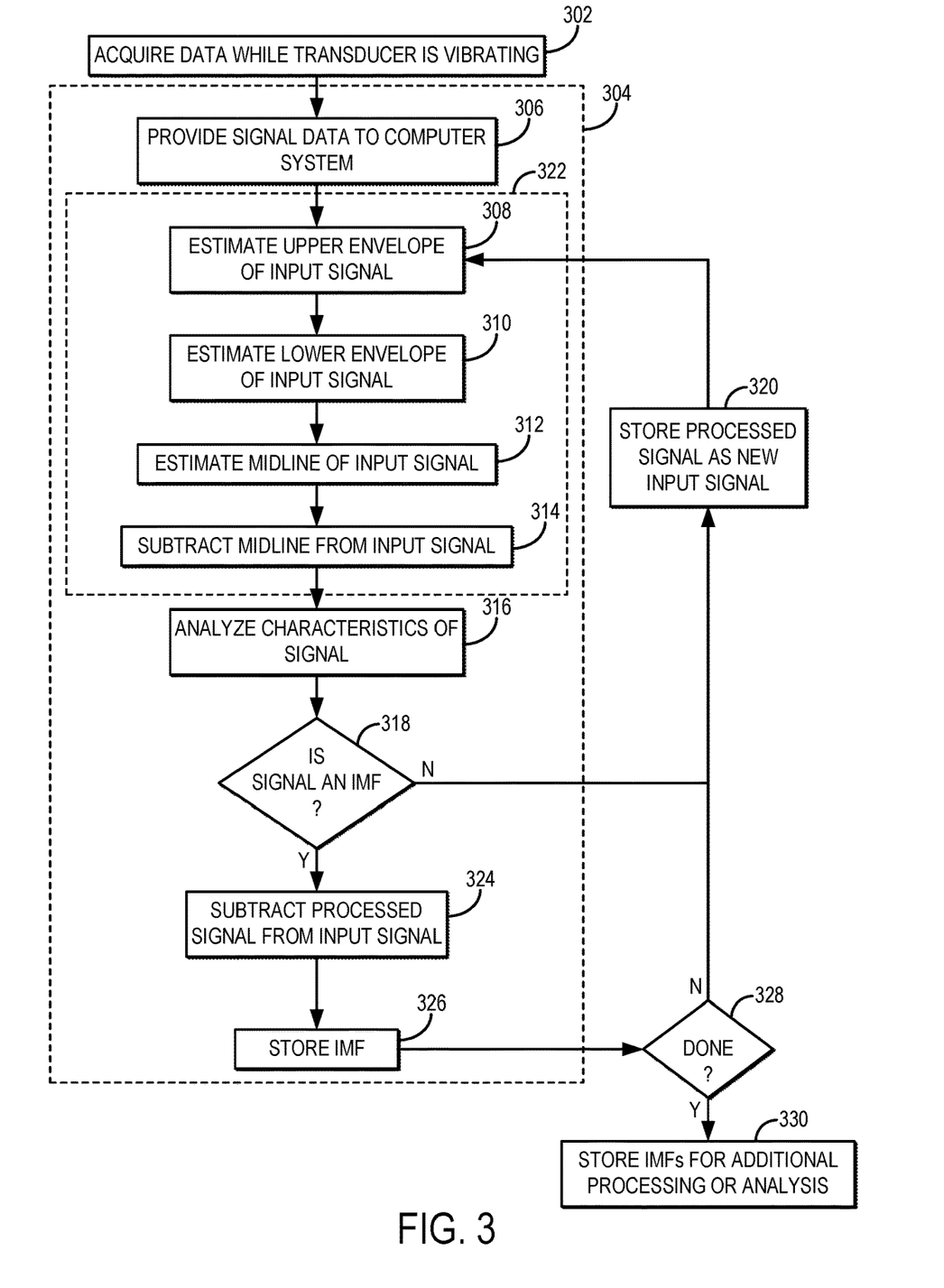
FIG. 3 is a flowchart setting forth the steps of an example method for separating shear wave signals from residual motion artifacts in data acquired using a continuously vibrating ultrasound transducer.

Referring now to FIG. 3, a flowchart is illustrated as setting forth the steps of an example method for extracting a shear wave signal, and thereby removing undesired effects of the continuous vibratory motion of the ultrasound transducer, using a modified EMD technique. The method generally includes acquiring data from an object using a transducer that is vibrating to generate shear waves in the object while the data are being acquired from the object, as indicated at step 302. The acquired data indicate the total, observed motion in the object. As will be described below in more detail, in some embodiments, the motion of the shear wave signals can be visualized in real-time. In general, the signal data includes a time series of real-valued data frames. After the data are acquired, they are processed using an EMD algorithm that is adapted to separate the shear wave signals from other motion signals (e.g., the motion of the vibrating transducer), as generally indicated at process block 304.

For the methods described in the present disclosure, two general modifications can be made to the EMD algorithm. First, a complex extension of EMD can be used to process the temporal harmonic of the signals in the acquired data at a particular frequency, obtained by performing a Fourier transform along the time dimension at each pixel. That is, rather than independently performing the EMD on the real and imaginary parts of the signals in the temporal harmonic of the acquired data, complex IMFs are estimated using information from both the real and imaginary components. This modification is useful when attempting to extract shear wave propagation with a single frequency. Second, the EMD processing can be modified from a one-dimensional processing to a higher dimensional processing, such as two-dimensional or three-dimensional processing, to account for spatial information contained within the wave field. As an example, a thin-plate spline can be used to estimate envelopes in 2D.

In general, the EMD algorithm separates non-stationary signals into multiple basis functions according to the inherent data structure of the signal. The method serves as a model-free approach to decompose complicated signals into intrinsic modes. This method functions by separating a signal into multiple intrinsic mode functions ("IMFs") that have at most one more zero crossing than local maxima and that are centered around zero such that the midpoint of the signal's envelope is equal to zero across the entire signal. These IMFs can be extracted from the parent signal through an iterative process of envelope fitting and signal separation. In some embodiments, the EMD can be implemented using a synchrosqueezed wavelet transform of the input signal data, as described by I. Daubechies, et al., in "Synchrosqueezed wavelet transforms: An empirical mode decomposition-like tool," *Applied and computational harmonic analysis,* 2011; 30(2):243-261.

Referring again to FIG. 3, the acquired data are processed using a modified EMD algorithm by first providing the signal data contained in the acquired data to a computer system, as indicated at step 306. For instance, the signal data can include a signal acquired with the ultrasound system while shear waves induced by continuous vibration of the ultrasound transducer were propagating in the subject.

In some embodiments, the signal data can be converted to complex-valued signal data. For instance, a Fourier transform can be applied to the signal data, which includes a time series of data frames, to extract complex-valued signal data for a single temporal frequency. The complex-valued signal data thus represents the motion in the subject (e.g., the shear wave and other motion) at that single frequency.

Advantageously, by converting the signal data to complex-valued signal data, shear wave signals with multiple different frequency components can be separately processed. For instance, the complex-valued signal data can be derived for a single frequency and processed as described below. The overall EMD process can then be repeated on additional complex-valued signal data that are derived from the input signal data for different frequencies.

An upper envelope is estimated from the input signal, as indicated at step 308. As an example, the upper envelope can be estimated by identifying all of the local maxima in the input signal and fitting a spline or other function through the identified points, or using an iterative constrained optimization procedure. A lower envelope is also estimated from the input signal, as indicated at step 310. The lower envelope can be estimated in a similar manner as the upper envelope. For instance, the lower envelope can be estimated by identifying all of the local minima in the input signal and fitting a spline or other function through the identified points, or using a constrained optimization procedure.

A midline of the input signal is estimated, as indicated at step 312. As an example, the midline can be estimated by calculating the mean of the upper and lower envelopes at each location. The midline is then subtracted from the input signal, as indicated at step 314, to effectively remove low frequency modulations from the input signal.

After the low frequency modulations have been removed from the input signal, the resulting signal is analyzed, as indicated at step 316. As one example, the number of zero crossings and local maxima can be identified again and analyzed. As another example, another metric can be analyzed. For instance, the change in the signal amplitude between consecutive sifts can be analyzed (e.g., using the standard deviation of the difference across the entire signal compared to a predetermined threshold). A determination is then made at decision block 318 whether the resultant signal is an IMF. As one example, if the number of local maxima exceeds the number of zero crossings by more than one, or if the midpoint of the envelope is not identically zero for all points, the resultant signal is not an IMF. In practice, it may not be feasible to obtain envelopes that result in identically zero midpoints. In such instances, this criterion can be relaxed such that the total deviations of the midpoints are smaller than a predefined threshold. The processed signal is then stored as a new input signal, as indicated at step 320, and a sifting process is initiated.

This sifting process is generally indicated by process block 322, which repeats the envelope detection and midline estimation and removal until both criteria are satisfied at decision block 318. When the signal is identified as an IMF at decision block 318, the IMF is subtracted from the original signal as indicated at step 324. The IMF is then stored as one of potentially multiple IMFs that can be extracted from the original signal, as indicated at step 326. As determined at decision block 328, when the resulting signal is monotonic within each data dimension and unable to be further decomposed, the EMD process is concluded and the one or more stored IMFs can be further processed or analyzed as desired, as indicated at step 330. If the criterion is not satisfied at decision block 328, the processed signal is stored as a new input signal at step 320 and the sifting process is repeated to extract additional IMFs, such as to extract shear wave motion signals corresponding to a compression profile.

In some instances, the IMFs can be processed to generate one or more images of the subject from which the signal data were acquired, in which the one or more images have reduced errors or artifacts associated with the vibration of the transducer. In some embodiments, the one or more images can depict shear wave motion occurring in the subject when the signal data were acquired. In some other embodiments, the one or more images can be mechanical, or material, property maps that depict a spatial distribution of mechanical, or material, properties of tissues in the subject from which the signal data were acquired. These mechanical property maps will have reduced errors or artifacts associated with the vibration of the transducer. Mechanical properties that can be computed from the IMFs, and therefore visualized in the mechanical property maps, include shear wave speed, strain, bulk modulus, shear modulus, viscosity, Young's modulus, and so on.

In the examples described above, a Fourier transform can be applied along the time dimension at each pixel to reduce the 3D data (e.g., 2D space and 1D in time) to 2D complex data for complex EMD processing, which saves computation time. However, the methods described above can also be applied to each individual time frame of real-valued data. The example described below with respect to FIGS. 4A-4D shows application to real-valued data in 1D.

Figures 4A, 4D:
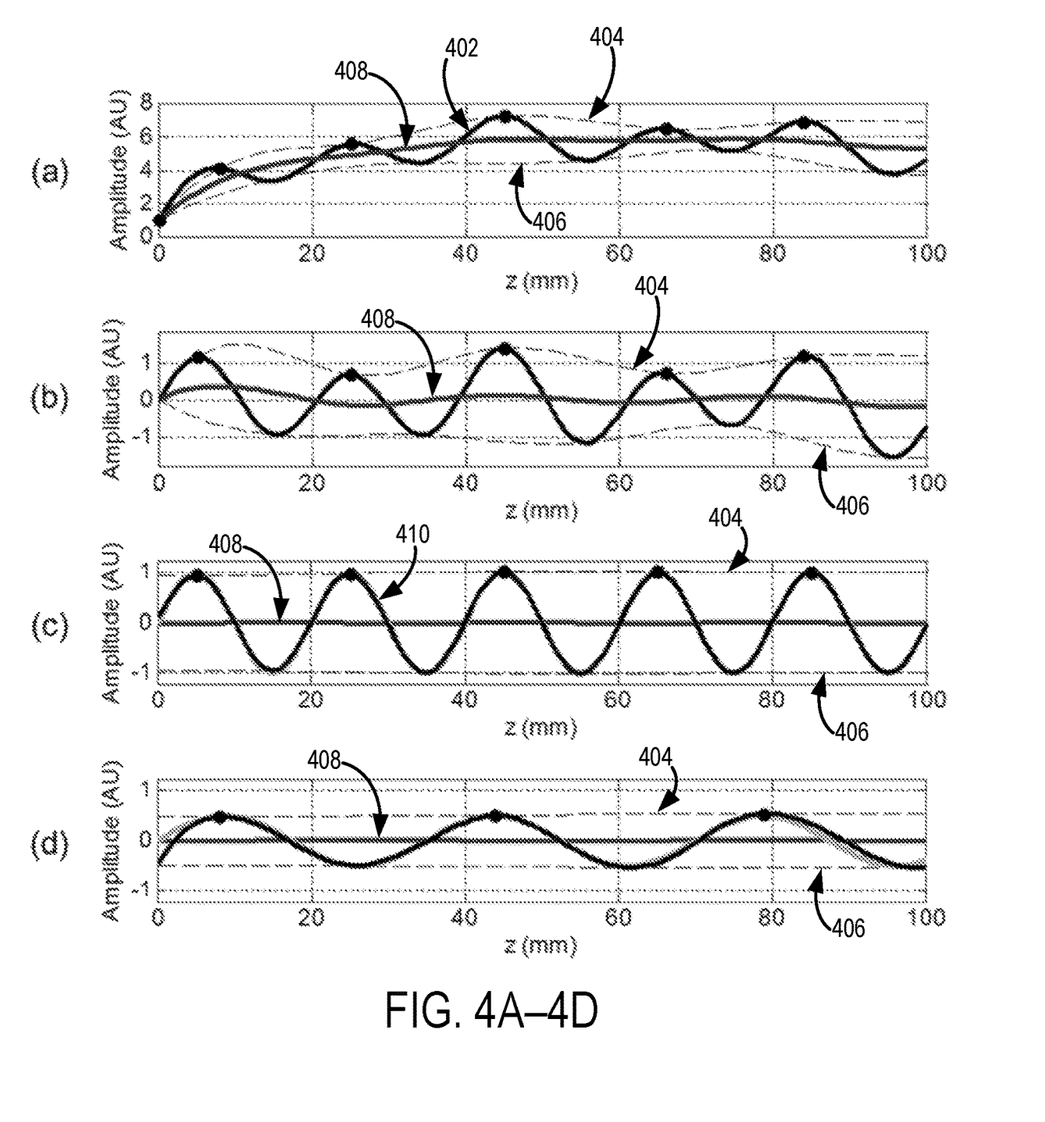

An example of the EMD process is illustrated in FIGS. 4A-4D. In this example, FIG. 4A shows a 1D numerical signal that contains two shear waves with amplitudes of 0.5 and 1, wavelengths of 20 and 35 mm, respectively, and a simulated compression with a maximum amplitude of 5 (black line 402). As described above, the EMD process begins by computing the upper and lower envelopes of the signal. The upper envelope 404 can be estimated by identifying all of the positive local maxima and fitting a spline through the resulting points. A similar process can be repeated to identify the lower envelope 406. Next, the midline 408 of the signal is obtained by calculating the mean of the two envelopes at each location. The midline is subtracted from the signal to effectively remove any low frequency modulations, the result of which is shown in FIG. 4B.

Once the modulations are removed, the number of zero crossings and local maxima are identified again. If the number of local maxima exceeds the number of zero crossings by more than one, or if the midpoint of the envelope is not identically zero for all points, the resultant signal is not an IMF, and a sifting process is initiated. This sifting process repeats the envelope detection and midline estimation/removal until both criteria are satisfied. In this example, the midline 408 of FIG. 4B has spatial variations requiring the iterative sifting process to be performed to obtain the IMF, which is shown as line 410 in FIG. 4C. Once an IMF is identified, it is subtracted from the original signal and the process is repeated until the input signal is monotonic and unable to be further decomposed. FIG. 4D shows the second IMF representing the second shear wave signal, with all additional IMFs corresponding to the compression. The ground truth signals for the IMFs in FIGS. 4C and 4D are shown as the gray signals in the respective figures.

The compression profile may be used to calculate additional mechanical properties of the tissue. For instance, the compression profile can be used to calculate the local strain or compression of the tissue. As the shear wave propagation speed of a material can change with compression, local strain and local shear wave speed, or other mechanical properties, can be measured simultaneously to evaluate the change of mechanical properties with different strain and compression. That is, non-linear mechanical properties can be measured and evaluated.

As mentioned above, in some embodiments the shear wave motion can be visualized in real-time using standard pulse-echo ultrasound. In these implementations, a real-time shear wave imaging sequence is utilized to provide visual feedback on shear wave quality, allowing the user to determine the best window for data collection.

Figure 5:
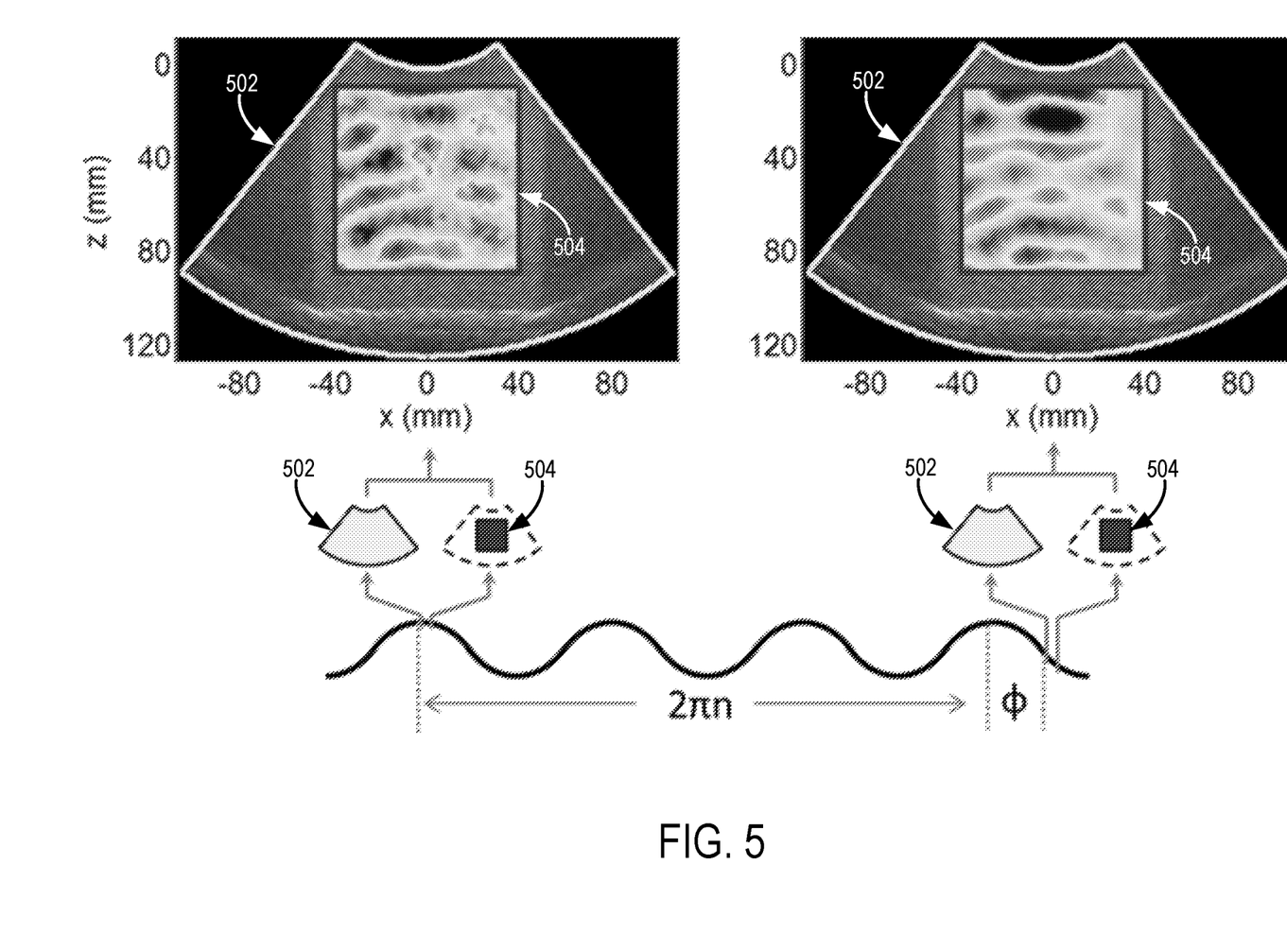
FIG. 5 depicts a timing diagram for real-time visualization of shear wave motion, which includes two detections separated by 1 ms. The first detection acquires a full field-of-view and is used for B-mode guidance. The second detection is a square field-of-view that is used to compute shear wave motion. The time required to process and display the image can be longer than a period; however, the periodic motion allows an integer number of cycles to be skipped before repeating the detection pairs to effectively sample every φ radians.

As one non-limiting example, the real-time visualization can implement an imaging sequence in which a pair of pulse-echo detections separated by a small time period are acquired. As one example, the small time period separating the pair of pulse-echo detection can be in the range of 0.1-10 ms, such as 1 ms. It will be appreciated that other separation time periods can be selected based on the frequency used for the pulse-echo ultrasound. The first detection can be a standard B-mode sector image acquired, for example, with planewave imaging using four angle compounding (e.g., −3°, −1°, 1°, and 3° steering angles). FIG. 5 shows an outlined field-of-view 502 of this detection. The second detection can still utilize planewave imaging of four angle compounding with the same steering angles, but with an acquisition and corresponding beamformed region that is limited to a smaller square region 504. The use of the smaller square area (instead of the full sector) for the second pulse echo event saves time in beamforming, which is important for real-time display. Shear wave motion can then be estimated for the smaller region 504. As one non-limiting example, Kasai's 1D autocorrelation method can be performed on the two detection frames to estimate shear wave motion. This method is descried by C. Kasai, et al., in "Real-time two-dimensional blood flow imaging using an autocorrelation technique," *IEEE Trans. on Sonics Ultrason.*, 1985; 32(3):458-464.

To better visualize the shear waves, a bandpass filter with cutoffs corresponding to shear wave speeds can be applied to the smaller, square region 504 to suppress probe motion artifacts, which appear as high speed components. For instance, the bandpass filter with spatial wavelength cutoffs corresponding to shear wave speeds of 0.5-6.0 m/s can be applied. As another example, a bandpass filter with spatial wavelength cutoffs corresponding to shear wave speeds upwards of 25 m/s can be applied. The latter examples can be useful for musculoskeletal applications where tendons or stiff muscles may be imaged or otherwise examined using the methods described in the present disclosure. Motion data in the square area 504 can be mirrored in both spatial dimensions before applying a Fourier transform (for bandpass filtering) to avoid boundary discontinuity artifacts. After frame-by-frame processing, the shear wave motion can be superimposed on the B-mode image and displayed in real-time on screen.

The approach described above interleaved B-mode and shear wave imaging to save computation time while providing real-time updates of a large sector B-mode image with a smaller (e.g., 8 cm by 8 cm) window display of shear waves. Implementation of this method can result in a display frame-rate of about 10 Hz.

In the event that the real-time visualization method described above is not able to directly image wave propagation (e.g., when the selected vibration frequency is higher than the display frame-rate), it is possible to leverage the periodic nature of the shear waves to track wave propagation. Because the probe's motion is periodic, the motion detected at a given phase will be identical to the motion detected when the phase differs by an integer number of periods. This relationship allows shear wave motion frames separated by a phase of $\phi$ to be visualized with detections spaced as $2\pi n+\phi$, where n is a positive integer. As one non-limiting example, n can be set such that there was a 100 ms delay between detections to allow sufficient time for beamforming, processing, and display of the previous shear wave frame. A schematic describing this acquisition timing is shown in FIG. 5.

When a suitable acoustic window is identified with the real-time shear wave visualization, the detection can be switched to an acquisition sequence that tracks motion across the full sector. As one example, acquisition across the full sector can be implemented by collecting 100 frames with four angle compounding (−3°, −1°, 1°, and 3° steering angles) at an effective frame-rate of 1 kHz.

The methods described in the present disclosure thus provide solutions to address challenges that arise when using PROSE for in vivo imaging: the identification of suitable imaging windows and the decoupling the shear waves from artifacts. The real-time display described above provides visual feedback, allowing the user to quickly survey multiple imaging windows. The modified EMD technique described in the present disclosure is able to successfully decouple the shear waves from artifacts related to the vibratory motion of the ultrasound transducer, and also allows accurate and stable shear wave speed estimates over a large field-of-view.

In the examples described above, planewave imaging with a high frame rate was used for motion detection. For ultrasound scanners with line-by-line scanning architecture, the time delays among different A-lines may need to be corrected. Time interpolation as proposed by P. Song, et al., in "Two-dimensional shear-wave elastography on conventional ultrasound scanners with time-aligned sequential tracking (TAST) and comb-push ultrasound shear elastography (CUSE)," *IEEE Trans Ultrason Ferroelectr Freq Control.*, 2015; 62 (2):290-302, can be used to account for this time delay. Alternatively, signals detected at different A-lines can be phase shifted to align in time, because the signals are sinusoidal, as described by A. Baghani, A. Brant, et al., in "A high-frame-rate ultrasound system for the study of tissue motions," *IEEE Trans. Ultrason. Ferroelectr. Freq. Control*, 2010; 57:1535-1547.

The complicated wave fields detected in PROSE from a continuously moving probe can be decoupled to isolate shear waves using the modified EMD methods described in the present disclosure. This can allow for stable reconstructions that are not affected by selection of bandpass filtering cutoffs. Thus, the methods described in the present disclosure provide for the application of PROSE as a 2D ultrasound elastography technology with the benefits of deep penetration, large field-of-view, and real time imaging.

In the examples given above, the modified EMD algorithm was applied to 2D spatial data (either real or complex data). It should be appreciated that the modified EMD algorithm can also be applied to a signal of any dimensionality, such as 1D or 3D spatial. Because the probe compression artifact mainly depends on depth, 1D EMD can be applied at each A-line along the depth direction to decouple shear wave signals from the compression artifacts.

Figure 6:
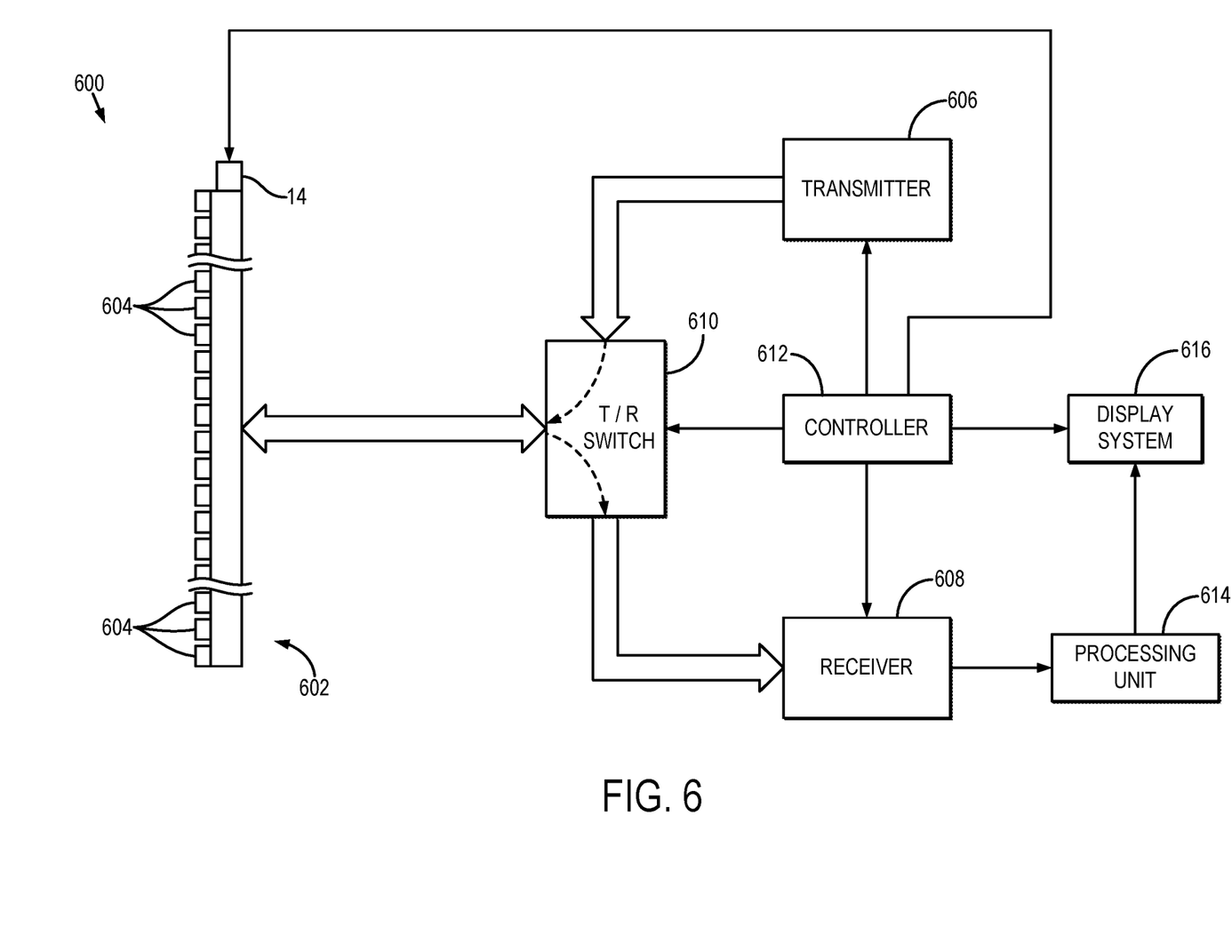
FIG. 6 is a block diagram of an example ultrasound system that can implement the methods described in the present disclosure.

FIG. 6 illustrates an example of an ultrasound system 600 that can implement the methods described in the present disclosure. The ultrasound system 600 includes a transducer array 602 that includes a plurality of separately driven transducer elements 604. The transducer array 602 can include any suitable ultrasound transducer array, including linear arrays, curved arrays, phased arrays, and so on. Similarly, the transducer array 602 can include a 1D transducer, a 1.5D transducer, a 1.75D transducer, a 2D transducer, and so on. As described above in more detail, an actuator 14 is coupled to the transducer array 602 and operated to vibrate the transducer array 602 to oscillate it in the axial direction.

When energized by a transmitter 606, a given transducer element 604 produces a burst of ultrasonic energy. The ultrasonic energy reflected back to the transducer array 602 (e.g., an echo) from the object or subject under study is converted to an electrical signal (e.g., an echo signal) by each transducer element 604 and can be applied separately to a receiver 608 through a set of switches 610. The transmitter 606, receiver 608, and switches 610 are operated under the control of a controller 612, which may include one or more processors. As one example, the controller 612 can include a computer system. As descried above, the controller 612 can also control the operation of the actuator 14. In some other embodiments, a separate controller can be used to control operation of the actuator 14.

The transmitter 606 can be programmed to transmit unfocused or focused ultrasound waves. In some configurations, the transmitter 606 can also be programmed to transmit diverged waves, spherical waves, cylindrical waves, plane waves, or combinations thereof. Furthermore, the transmitter 606 can be programmed to transmit spatially or temporally encoded pulses.

The receiver 608 can be programmed to implement a suitable detection sequence for the imaging task at hand. In some embodiments, the detection sequence can include one or more of line-by-line scanning, compounding plane wave imaging, synthetic aperture imaging, and compounding diverging beam imaging.

In some configurations, the transmitter 606 and the receiver 608 can be programmed to implement a high frame rate. For instance, a frame rate associated with an acquisition pulse repetition frequency ("PRF") of at least 100 Hz can be implemented. In some configurations, the ultrasound system 600 can sample and store at least one hundred ensembles of echo signals in the temporal direction.

The controller 612 can be programmed to design and implement imaging sequence using the techniques described in the present disclosure, or as otherwise known in the art. In some embodiments, the controller 612 receives user inputs defining various factors used in the design of the imaging sequence.

A scan can be performed by setting the switches 610 to their transmit position, thereby directing the transmitter 606 to be turned on momentarily to energize transducer elements 604 during a single transmission event according to the designed imaging sequence. The switches 610 can then be set to their receive position and the subsequent echo signals produced by the transducer elements 604 in response to one or more detected echoes are measured and applied to the receiver 608. The separate echo signals from the transducer elements 604 can be combined in the receiver 608 to produce a single echo signal.

The echo signals are communicated to a processing unit 614, which may be implemented by a hardware processor and memory, to process echo signals or images generated from echo signals. As an example, the processing unit 614 can extract shear wave motion signals and compression profiles, from which mechanical properties can be estimated, using the methods described in the present disclosure. Images produced from the echo signals by the processing unit 614 can be displayed on a display system 616.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for ultrasound elastography using a continuously vibrated ultrasound transducer, the steps of the method comprising:
    (a) providing a continuous vibration to an ultrasound transducer, whereby vibration of the ultrasound transducer induces a shear wave in an object;
    (b) acquiring signal data from the object using the ultrasound transducer, wherein the signal data are indicative of the shear wave propagating within the object;
    (c) processing the signal data by:
    converting the signal data to a complex representation of motion at a single temporal frequency by applying a Fourier transform to the signal data along a time dimension, generating output as a complex-valued signal data; and
    using an empirical mode decomposition to extract an intrinsic mode function (IMF) from the complex-valued signal data, wherein the IMF represents motion of the shear wave in the object that has been separated from motion associated with the vibration provided to the ultrasound transducer; and
    (d) storing the IMF as shear wave signal data indicative of shear wave motion at a single temporal frequency.

2. The method as recited in claim 1, wherein converting the signal data to complex-valued signal data is repeated for each of a plurality of different temporal frequencies to generate a respective plurality of different complex-signal data, and steps (c) and (d) are repeated for each of the plurality of different complex-signal data in order to extract and store a different IMF for each of the plurality of different complex-valued signal data.

3. The method as recited in claim 1, wherein the empirical mode decomposition estimates a two-dimensional upper envelope and a two-dimensional lower envelope from the signal data, and the IMF is extracted based at least in part on the two-dimensional upper envelope and the two-dimensional lower envelope.

4. The method as recited in claim 3, wherein the two-dimensional upper envelope and the two-dimensional lower envelope are estimated using a thin-plate spline.

5. The method as recited in claim 3, wherein the two-dimensional upper envelope and the two-dimensional lower envelope are estimated using an external value-constrained optimization procedure that iteratively identifies a smooth envelope function.

6. The method as recited in claim 3, wherein the empirical mode decomposition estimates a midline based on the two-dimensional upper envelope and the two-dimensional lower envelope and subtracts the midline from the signal data to estimate the IMF.

7. The method as recited in claim 6, wherein the midline is estimated at each location by computing a mean of the two-dimensional upper envelope and the two-dimensional lower envelope at each location.

8. The method as recited in claim 6, wherein the IMF is stored as the shear wave signal data when a characteristic of the IMF satisfies a specified criterion, and the IMF is sifted to further remove low frequency modulations when the characteristic of the IMF does not satisfy the specified criterion.

9. The method as recited in claim 8, wherein the IMF is sifted by estimating an updated two-dimensional upper envelope and an updated two-dimensional lower envelope from the IMF, estimating an updated midline from the updated two-dimensional upper envelope and the updated two-dimensional lower envelope, and subtracting the updated midline from the IMF.

10. The method as recited in claim 8, wherein the stored IMF is stored as a first IMF and further comprising estimating a second IMF by sifting the first IMF, wherein the second IMF is indicative of shear wave motion occurring at a different frequency than the shear wave motion indicated by the first IMF.

11. The method as recited in claim 8, wherein the stored IMF is stored as a first IMF and further comprising estimating a second IMF by sifting the first IMF, wherein the second IMF is indicative of a compression profile associated with compression caused by the continuous vibration provided to the ultrasound transducer.

12. The method as recited in claim 11, further comprising computing a mechanical property using the compression profile.

13. The method as recited in claim 1, wherein step (b) comprises visualizing shear wave motion in the object using an imaging sequence comprising:
   acquiring B-mode image data over a large field-of-view in the object; and
   acquiring beamformed image data over a small field-of-view that is smaller than and contained within the large field-of-view; and
   wherein step (b) includes acquiring the signal data from the large field-of-view when shear wave motion estimated from the beamformed image data over the small field-of-view satisfies a detection criterion.

14. The method as recited in claim 13, wherein the B-mode image data and the beamformed image data are acquired over a pair of pulse-echo ultrasound detections that are separated in time by a duration of time.

15. The method as recited in claim 14, wherein the duration of time is selected from a range of 0.1 milliseconds to 10 milliseconds.

16. The method as recited in claim 13, wherein the beamformed image data are filtered using a bandpass filter with cutoff values corresponding to spatial wavelengths associated with shear wave speeds.

17. The method as recited in claim 16, wherein the cutoff values are selected based on spatial wavelengths associated with shear wave speeds in a range of 0.5 to 6.0 meters per second.

18. The method as recited in claim 1, further comprising estimating one or more mechanical property values of the object from the shear wave signal data.

19. The method as recited in claim 18, further comprising generating a mechanical property map from the one or more mechanical property values, wherein the mechanical property map depicts a spatial distribution of mechanical property values in the object.

20. The method as recited in claim 1, further comprising generating an image from the shear wave signal data, wherein the image depicts a visual representation indicating shear wave motion in the object separate from the vibration provided to the ultrasound transducer.

21. The method as recited in claim 1, wherein the empirical mode decomposition is constructed using a synchrosqueezed wavelet transform of the signal data.

* * * * *